(12) United States Patent
Anderson

(10) Patent No.: US 7,069,771 B1
(45) Date of Patent: Jul. 4, 2006

(54) PARTITIONING SEDIMENT TRAP

(76) Inventor: Roger Yates Anderson, 5014 Guadalupe Trail NW., Albuquerque, NM (US) 87107

( * ) Notice: Subject to any disclaimer, the term of this patent is extended or adjusted under 35 U.S.C. 154(b) by 0 days.

(21) Appl. No.: 11/054,016

(22) Filed: Feb. 9, 2005

(51) Int. Cl.
*G01N 15/04* (2006.01)
(52) U.S. Cl. .................................. 73/61.65; 73/170.32
(58) Field of Classification Search ............... 73/61.63, 73/61.65, 61.66, 61.68, 170.32, 863.21, 864.73
See application file for complete search history.

(56) References Cited

U.S. PATENT DOCUMENTS 3,715,913 A    2/1973   Anderson
3,869,903 A *  3/1975   Beach et al. ............... 73/61.65
4,321,823 A    3/1982   Anderson

* cited by examiner

*Primary Examiner*—Charles Garber

(57) ABSTRACT

A partitioning sediment trap adapted to be positioned in a body of water comprising an elongate, vertically alignable transparent collecting tube having an open upper end and a closed lower end for collecting, over a longer period of time, natural materials, contaminants, and polluting substances that accumulate in the body of water. A generally funnel-shaped cone is positioned with the small diameter end thereof extending into the open end of the collecting tube to magnify the amount of material collected. Means are also provided for automatically and efficiently partitioning and isolating undisturbed material accumulated in the collecting tube at regular time intervals.

20 Claims, 3 Drawing Sheets

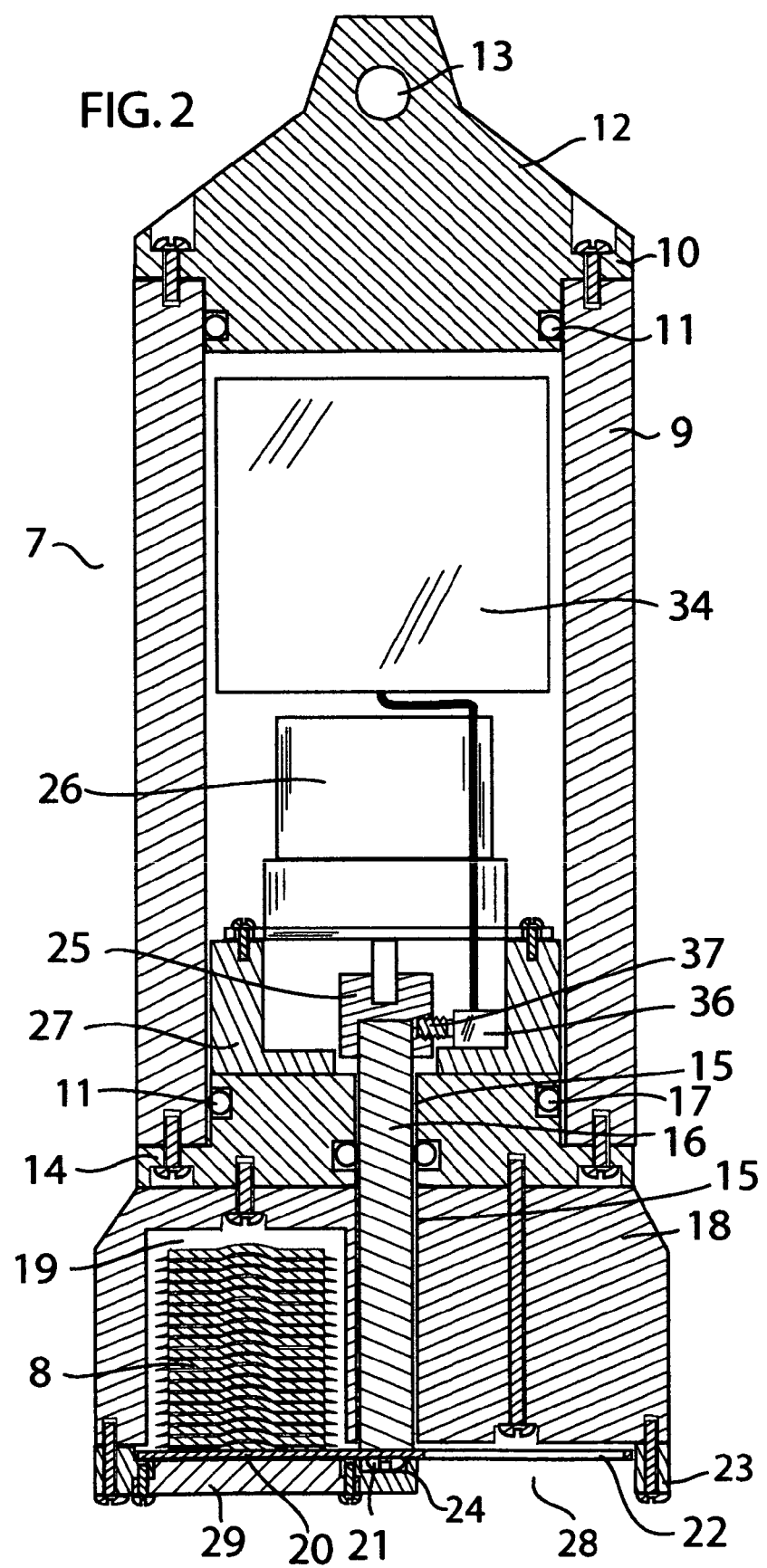

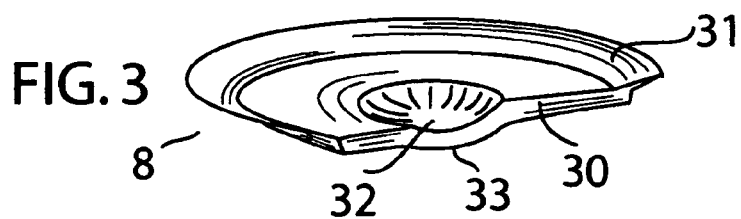

PARTITIONING SEDIMENT TRAP

CROSS-REFERENCE TO RELATED APPLICATIONS

The above titled application is a significant improvement upon prior patents U.S. Pat. No. 3,715,913 (Aquatic Sediment and Pollution Monitor), and U.S. Pat. No. 4,321,823 (Aquatic Sediment and Current Monitor) previously issued to the above applicant. The above titled application is not related to or referenced to any other prior or pending applications.

FEDERAL SPONSORSHIP

Not Applicable.

SEQUENCE LISTING OR PROGRAM

Not Applicable

BACKGROUND OF INVENTION

1. Field of Invention

The present invention relates to the collection and measurement of natural materials, contaminants, and polluting substances that accumulate in aquatic environments such as lakes, reservoirs, oceans, estuaries, and other bodies of water, and, more particularly, to apparatus positioned within bodies of water to automatically collect such materials and substances for the purpose of determining composition, rates of movement, and the general condition of water bodies.

2. Description of Prior Art

Devices referred to generally as time-series sediment traps have found widespread application in measuring the abundance of lacustrine and marine organisms such as bacteria, algae, other phytoplankton, and zooplankton. Such trapping devices have also been employed to determine the volume and flux of suspended particles such as silt, clay, and fragments of organic matter and various contaminants and polluting substances contained within or adhering to such particles. In addition, time-series sediment traps have been used to determine the point sources of natural and introduced particles as well as the time when such materials reached the location of a deployed device. Also, time-series sediment traps have been used in a wide range of scientific investigations such as the Joint Global Ocean Flux Study, an international global program to measure the flux of particles to the sea floor. Such investigations are an essential aspect of estimating the global cycling of carbon, which is related to environmental problems such as global warming. Other scientific investigations are concerned with particle movement during storms, tsunamis, and submarine landslides. Over the last three decades such devices have become a standard tool for investigating specific aquatic events, tracing pathways of pollution, and monitoring changing conditions in lakes, oceans, and estuaries.

Time-series sediment traps employ a cone or funnel to greatly magnify the volume of material that settles in collecting chambers and they also provide a means for collecting materials at regular time intervals. One such time-series device, developed by the present inventor, collected materials in a single, long collecting tube and marked the time intervals by periodically dropping plastic granules into the collecting tube. The present inventor was granted a utility patent for this device in 1973 by the U.S. Patent Office (U.S. Pat. No. 3,715,913, now in the public domain). This device was used in various investigations by research scientists, environmental contractors, and government agencies. Although the simple device provided by U.S. Pat. No. 3,715,913 was effective in certain situations, a failure of the marking system to isolate settled materials under some common conditions restricted its use to a limited number of applications. The problem is traceable to the granules of TEFLON® that were employed to mark time intervals. For example, if settled materials had a high fluid content, the granules settled differentially to form a poorly defined marking layer. If rates of accumulation were low, two or more marking layers were indistinguishable. A slight and often unavoidable tilting of the collecting tube after deployment resulted in the streaming of granules down one side of the collecting tube, resulting in failure to identify a time-marked interval. Upon recovery of the collecting tube uncertain boundaries between layers of granules limited the accuracy of sampling. In addition, granules required removal from a sample before measuring the volume and weight of recovered materials, but other materials were removed also, distorting the measurements of volume and bulk density.

The above-cited problems of an automated method for collecting aquatic materials in a single collecting tube by periodically releasing granules from a dispensing device limited the use of the method and favored a trap design in which materials are collected in individual bottles that are automatically and sequentially rotated below the narrow open end of a funnel. Although most time-series trap investigations now collect samples in many separate wide-mouth bottles or cups, this currently favored method has serious limitations. Among problems of collecting materials in multiple bottles is a failure to provide uninterrupted and undisturbed records of sediment accumulation. Continuous records of events talking place in water bodies are highly desirable because many such events are short-lived and are accompanied by abrupt changes in color, texture and composition of materials. For example, the effects of storm events, by flushing coarse particles from stream channels and by re-suspending already accumulated bottom sediments are well known, and are accompanied by changes in the physical and chemical properties of materials collected in funnel-shaped traps. Indeed, these same textural and composition changes in the water bodies are magnified in cone-shaped traps and clearly revealed in single, elongate collecting tubes. In another example, sewage outfall after heavy rains often contains contaminating substances that are confined to a "spike" and are thereafter dissipated. However, the current practice of collecting such evidence in many wide-mouth bottles or cups, and the unavoidable disturbance of collected materials during recovery fails to preserve evidence for such short-lived events. A single rotated vessel, for example, commonly collects material in 30-day intervals. But a single event such as a pollution episode may occur both before and after vessels are exchanged, thereby providing only a 60-day resolution for an event that occurred within one or a few days.

All of the problems and limitations of currently deployed, funnel-shaped, multiple-vessel, sediment trapping devices, with respect to loss of continuity and preservation of structures, textures, and composition are overcome by providing an innovative and major improvement in the method of isolating aquatic materials collected in an elongate vessel. Not only does the present invention replace the need for collecting samples in many rotated vessels, it overcomes all of the problems specific to such vessels, as well as all of the problems and disadvantages previously encountered with devices that mark regular time intervals in a single, elongate collecting tube.

SUMMARY OF INVENTION

According to the present invention, there is provided an apparatus that overcomes the problems discussed above with respect to prior art systems. According to the present invention, a single, elongate, vertically aligned, and transparent tube constructed of polycarbonate, closed at the lower end and open at the upper end, is positioned at the open end to receive the narrow opening of a funnel and the apparatus is placed in a body of water for a long period of time to collect a continuous record of particulate materials. A device positioned within the funnel, hereinafter referred to as a dispensing device, is programmed to release thin, solid partitions at known time intervals, thereby effectively isolating materials that accumulate within the elongate collecting vessel and at the same time preserving textures and structures of accumulated material.

Materials that accumulate in the collecting vessel are separated from materials that accumulate during previous and later time intervals by circular, boat-shaped hydrodynamic partitions composed of inert plastic material. Partitions have a high specific gravity (2.16) and are provided with a navicular shape that assures a controlled descent and horizontal orientation within the funnel and within the vertically aligned collecting tube. The rate of descent of the partitioning device is further controlled by providing an appropriate diameter for the partition relative to the inner diameter of the collecting vessel, thereby the partition settles slowly and gently in a horizontal position on the upper surface of previously accumulated and undisturbed materials.

OBJECTS, FEATURES, AND ADVANTAGES

It is therefore the object of the present invention to solve the problems encountered heretofore with the automated collection of suspended materials in bodies of water in a predetermined time series. It is a feature of this invention to solve these problems by amplifying the settling rate of particulate materials, by continuously accumulating such materials in a single vessel, by preserving the structures and textures imparted to such materials by processes operating within a water body, and by effectively isolating accumulations of particulate material in predetermined time intervals.

The present invention, by employing a navicular partition to isolate intervals of particulate material, overcomes the disadvantages of previous devices by isolating the accumulated material with solid, horizontally emplaced partitions. Whereas a flat disk falls edgewise in a vertical collecting tube at rates exceeding 20 cm/second and lodges in underlying accumulated particles, a navicular partition maintains a generally horizontal orientation and settles in the collecting tube at about 1 cm/second. The rate of settling is regulated by changing the space between the navicular partition and the inner wall of the collecting tube, thereby controlling the upward escape of water displaced by the descending partition. As a result, the partition comes to rest gently and horizontally on the upper surface of previously settled and undisturbed particles. Not only are underlying particles essentially undisturbed, the hydrodynamic form of the navicular partition provides a small chamber for the isolation of particles even when the rate of particle accumulation is extremely low.

Critical to certain investigations in aquatic environments are undisturbed structures, textures, and compositional differences that are the result of events taking place in the water body. For example, a thin layer of coarse and fine particles, positioned above the first-emplaced partition in FIG. 1B of the drawings, reveals textural changes typical of those preserved in a transparent and elongate collecting tube after a brief storm. Such features provide for the detailed examination and interpretation of events in a water body through the preservation of features such as particle color, composition, size, texture, and structure. Hence, the effects of currents, storms, tsunamis, sewage outfall, plankton blooms, dredging, and other events occurring in water bodies can be traced to known causes, and the timing of such events can be more precisely determined by noting the position of such features relative to partitions emplaced at known time intervals.

The combination of a magnified rate of particle accumulation in a single elongate collecting tube and isolating such materials with solid partitions provides a means for sampling and analyzing specific, short-term events in water bodies. For example, high concentrations of contaminating substances are commonly restricted to a particular layer, color, or texture found between partitions emplaced at known time intervals. These delicate layers and features are commonly destroyed by during recovery operations if collected in wide-mouth bottles in which materials necessarily have a high fluid content. In contrast, materials collected in a single tube and separated by navicular partitions become dewatered and compacted over time, thereby preserving delicate features for later examination and analysis. In fact, delicate structures remain undisturbed in elongate tubes that are recovered and transported in a nearly horizontal position. Hence, the combined use of navicular partitions and a single transparent collecting tube represents a significant improvement over prior art methods of automatically collecting materials suspended in water bodies.

Still another advantage of the present invention is the small size and simple design of the dispensing device, as compared to more complex apparatus that employ multiple collecting vessels. Furthermore, the behavior of navicular partitions is independent of size and diameter and is therefore adaptable to a wide range of funnel sizes, collecting tube diameters, ratios of magnification, and conditions of deployment, thereby potentially extending applications of the method and expanding investigations of environmental problems in water bodies.

Still other objects, features, and advantages of the present invention will become apparent to those skilled in the art from a reading of the following detailed description of the preferred embodiment and the accompanying drawings, wherein like numerals designate like parts in the several figures:

BRIEF DESCRIPTION OF THE DRAWINGS

FIG. 2 is an enlarged sectional view taken through the center of the dispensing device incorporated within the structure of FIG. 1;

FIG. 3 is a perspective view, partly cut away, of the partitioning navicular structure released from the dispensing device of FIG. 1 and FIG. 2;

FIG. 4A and FIG. 4B are enlarged sectional views of a portion of dispensing device of FIG. 2; and FIG. 5A and FIG. 5B are perspective views of a portion of dispensing device of FIG. 2.

DESCRIPTION OF THE PREFERRED EMBODIMENT

Figure 1A:
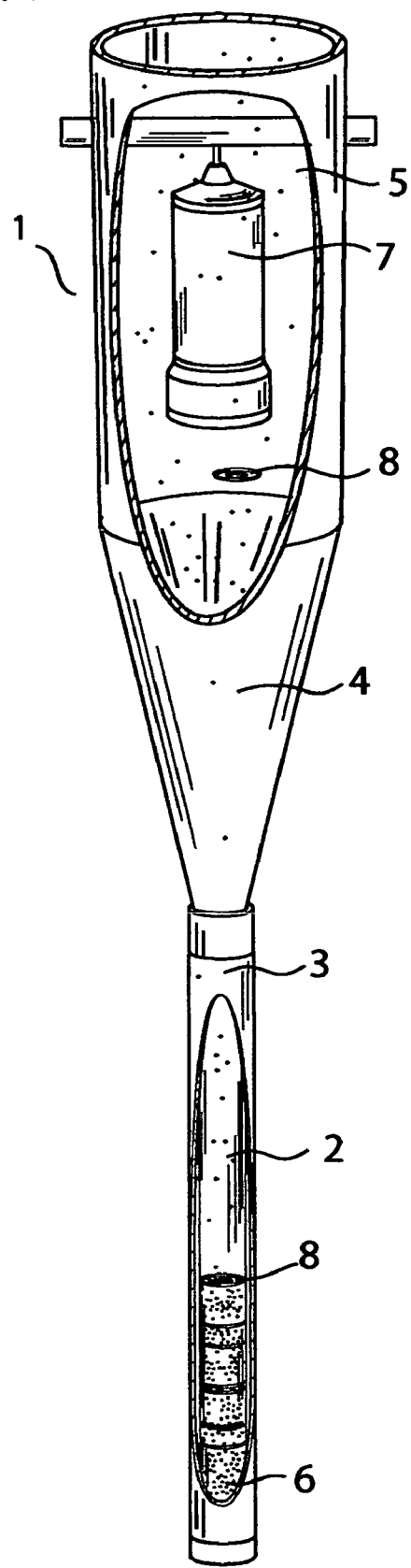
FIG. 1A is an isometric view, partly cut away, of a preferred embodiment of a partitioning sediment trap.
Figure 1B:
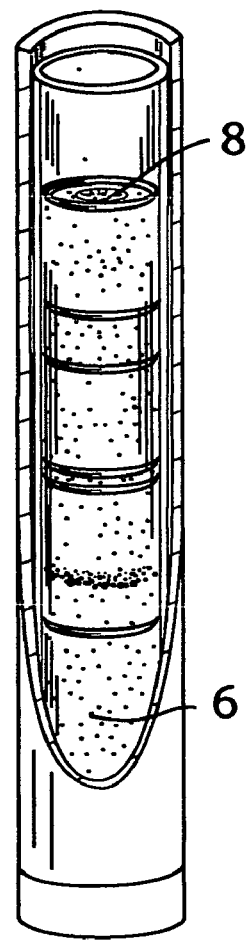
FIG. 1B is an enlarged view of the lower portion of FIG. 1A.

Referring now to FIGS. 1A and 1B of the drawings, there is shown a partitioning sediment trap, generally designated 1, which has several components in common with the aquatic sediment and pollution monitor described and claimed in my prior U.S. Pat. No. 3,715,913. More specifically, partitioning sediment trap 1 includes a collecting tube 2 having an open upper end and a closed lower end for collecting and storing, over a relatively long period of time, materials, contaminants, and pollutants in a water body. Collecting tube 2 is positioned within a housing tube 3 which is connected adjacent the small diameter end of a cone 4 that magnifies the rate of accumulation of suspended particles 5. The small diameter end of the magnifying cone 4 extends into the collecting tube 2, which is held in position by the housing tube 3. Suspended particles 5 in the water body entering the large diameter opening of the magnifying cone 4 come to rest as settled particles 6 above the lower closed end of the collecting tube 2.

According to the preferred embodiment of the present invention, partitioning sediment trap 1 includes a dispensing device 7 for automatically marking, at regular intervals, the quantity of sediment accumulated in collecting tube 2 during such intervals. According to the embodiment of FIG. 1A, dispensing device 7 is positioned within a cylindrical extension of the upper part of magnifying cone 4. As will be discussed in greater detail hereinafter, and illustrated in FIG. 2, dispensing device, generally designated 7, includes a magazine chamber 19 containing many navicular partition structures 8 having a density greater than water. Rotation of a large-diameter chamber, hereinafter designated a partition trap 22, configured as an integral part of a rotor 20, transfers a partition 8 from the magazine chamber 19 to partition trap 22 positioned below and aligned with magazine chamber 19. Further rotation transfers partition to a release chamber 28 whereupon the partition 8 descends in a controlled manner, passes through the lower, small opening of the magnifying cone 4 and comes to rest horizontally on the upper surface of previously accumulated particles 6 within the collecting tube 2. Means to rotate the rotor 20 at regular time intervals and a plurality of partitions 8 within the magazine chamber 19 thereby provide partitions between accumulated particles 6 for many known time intervals. Later recovery of the partitioning sediment trap 1 provides sufficient material for collection and analysis for which the precise time of accumulation is known.

Referring now to FIG. 2, a preferred embodiment of dispensing device 7 includes a tubular body 9 constructed of material with sufficient strength to resist pressure. The upper end of the tubular body 9 is terminated by an upper cap 10, which is sealed with a static o-ring 11 and secured to the tubular body 9 by appropriate machine screws. A conical shield 12 is an integral part of the upper cap 10, near the top of which is provided a hole 13 of sufficient diameter to suspend the dispensing device 7 from a supporting structure within the cylindrical extension of magnifying cone 4. The lower end of the tubular body 9 is closed by a lower cap 14, which is sealed within the tubular body 9 by a static o-ring 11. The center of the lower cap is provided with a shaft hole 15 for receiving a rotating shaft 16, which is sealed within the lower cap 14 by a dynamic o-ring 17. The static o-rings 11 and the dynamic o-ring 17 provide seals that assure a water-tight interior within the tubular body 9 when submerged under high pressure.

Referring again to FIG. 2, a cylindrical magazine block 18 is provided with a centrally positioned shaft hole 15, and a cylindrical magazine chamber 19 is provided between the shaft hole 15 and the outer diameter of the magazine block 18. The magazine block 18 is positioned adjacent to the lower, outer surface of the lower cap 14 and bolted to the cap 14 with appropriate machine screws. The shaft 16 is attached to a circular rotor 20, which contains the partition trap 22, and rotor is secured to shaft by a rotor mounting screw 21.

Referring once again to FIG. 2, the rotor assembly 16, 20, 21 is positioned within the shaft hole 15 aligned with the center of a cylindrical magazine cap 23, which is provided with a central screw-head chamber 24 for receiving the head of the mounting screw 21 of aforementioned rotor assembly. A connector 25 at the upper end of shaft 16 connects the shaft to the drive shaft of a direct current gearmotor 26 aligned with the axis of shaft 16 and bolted to a mounting block 27 by appropriate machine screws. The magazine cap 23 is provided with a large opening herinafter referred to as a release chamber 28, of the same planar dimensions as the partition trap 22 and positioned 180 degrees with respect to axis of shaft hole 15 and magazine chamber 19. Prior to use, partitions 8 are placed within magazine chamber 19 by removing a large circular plug 29 in the magazine cap 23 that is held in place by appropriate machine screws.

Referring specifically to FIG. 3, a navicular partition, generally designated 8, has a circular outline in plan view. The partition 8 is constructed to provide an inner body 30 from which projects a thin, upward-directed flange 31 around the perimeter of inner body 30. A depression 32 and dome 33 in the central portion of inner body 30 are constructed to have the same vertical thickness dimension above inner body 30 as the vertical thickness of flange 31 below inner body 30 in sectional view, thereby providing a partition 8 having a generally navicular shape for which the convex surface is directed downward and concave surface and flange 31 are directed upward during free-fall through water within the magnifying cone 4 and collecting tube 2.

Referring to FIGS. 2 and 4A, and to the operation of the dispensing device 7, the lowermost of a plurality of navicular partitions 8 within the magazine chamber 19 rests within the partition trap 22 at the start of a dispensing cycle. Commercially available electronic timing circuitry and battery power 34 housed inside the water-tight tubular body 9 of the dispensing device 7 sends an electrical current through the closed pole of a commercially available microswitch 35, thereby turning the gearmotor 26, connector 25, shaft 16, rotor 20 and integral partition trap 22 containing the lowermost partition 8 previously placed in magazine chamber 19. Rotation of the rotor 20 and leading edge of partition trap 22 engages the edge of lowermost partition, which is transferred to the release chamber 28 upon rotation of 180 degrees.

Referring to FIG. 4B, there is provided a single deflector 35 positioned opposite the direction of motion of rotor 20, projecting part way into release chamber 28, and affixed to lower surface of magazine cap 23 by appropriate machine screws. Referring to FIGS. 4B, 5A, and 5B, partition 8 is transferred to release chamber 28 by rotary motion of partition trap 22 and thereafter is directed downward by force of gravity and strikes deflector 35, thereby titling partition, accelerating downward movement and application of hydrodynamic forces, whereupon partition 8 becomes hydrodynamically stable when the convex surface reaches a convex-downward horizontal orientation after a free fall of about 15 centimeters. Partition 8 descends in magnifying cone 4 in a generally horizontal orientation with the dome 33 facing downward and enters the collecting tube 2 in the same orientation. Thereafter, rate of descent of navicular partition 8 in collecting tube 2 is retarded by upward flow of water between solid partition 8 and inner wall of collecting tube 2 and partition comes to rest horizontally on upper surface of previously settled particles 6.

Referring again to FIGS. 2 and 1, continued closure of electrical circuit and operation of gearmotor 26 rotates shaft connector 25 until microswitch 36 acted upon by continued rotation of timing cam 37 interrupts electrical circuit after particle trap 22 completes a 360-degree rotation and is repositioned below the magazine chamber 19. Gravity acting upon other partitions 8 in magazine chamber 19 automatically moves the lowermost partition 8 into partition trap 22, completing a cycle of operation. Continued operation of timing circuitry 34 periodically activates subsequent cycles and provides the release of additional partitions 8 and collection of suspended particles 5, 6 in a time series.

It can, therefore, be seen that in accordance with the present invention there is provided an efficient apparatus for magnifying, collecting, and determining the volume or quantity of natural materials, contaminants, and polluting substances suspended in water bodies. The present partitioning sediment trap serves to completely replace inefficient structures of prior art collecting and measuring methods. Not only is the present apparatus more efficient in isolating materials that accumulate in a single, elongate vessel, employment of boat-shaped partitions completely eliminates uncertainty in the timing of collection intervals. Furthermore, the specific gravity and hydrodynamic properties of the isolating partitions provides for the controlled descent of separating discs and providing gentle and horizontal emplacement of separating layers without disturbing previously accumulated materials and structures. Dewatering of materials in a single tube containing partitions prevents disturbance of original structures. In addition, use of solid partitions eliminates problems associated with the removal of marking materials before analysis. Importantly, the present invention, by employing a single transparent collecting tube, in conjunction with the gentle emplacement of solid partitions, provides for both the collection of materials in a time series and the preservation of physical features imparted to such materials by events taking place in a water body. The improved method provides a simple, inexpensive automatic dispensing device for a wide range of applications whereby aquatic materials are collected in a time series, thereby potentially increasing the number and scope of investigations pertaining to the general health and use of water bodies.

While the invention has been described with respect to a preferred physical embodiment constructed in accordance therewith, it will be apparent to those skilled in the art that various modifications and improvement may be made without departing from the scope and spirit of the invention. Accordingly, it is to be understood that the invention is not to be limited by the specific illustrative embodiment, but only by the scope of the appended claims.

I claim:

1. A partitioning sediment trap adapted to be positioned in a body of water comprising:
    an elongate, vertically alignable, transparent collecting tube having an open upper end and a closed lower end for containing accumulated particles in said water body;
    a generally funnel-shaped magnifying cone positioned with the small diameter end thereof extending into said open end of said transparent collecting tube for magnifying number of said particles in said collecting tube;
    a plurality of planar partitions for separating said particles in said collecting tube;
    an automatic dispensing device containing plurality of said partitions positioned to release single said partitions into said magnifying cone at predetermined time intervals;
    means for emplacing said partitions in a generally horizontal position on surface of said accumulated particles in said collecting tube.

2. the partitioning sediment trap of claim 1, wherein said means for emplacing said partitions in said horizontal position comprises:
    a planer partition exceeding the specific gravity of water;
    a generally concave surface on one planar side of said partition;
    a generally convex surface on opposing side of said partition;
    gravitational force means and resistance to hydraulic pressure means for positioning said partition in a generally horizontal position on surface of said accumulated particles in said collecting tube.

3. the partitioning sediment trap of claim 2 wherein said partition comprises;
    material of high specific gravity;
    whereby said material of high specific gravity has proportionately greater rate of descent thereby providing proportionately greater hydraulic pressure to said partition.

4. the partitioning sediment trap of claim 2 wherein said partition comprises;
    material having self-lubricating properties;
    whereby said self-lubricating properties of said partition provides low friction means for moving said partitions in said dispensing device.

5. the partitioning sediment trap of claim 1, wherein emplacing said partition in said horizontal orientation comprises:
    a generally navicular partition composed of material with high specific gravity;
    natural gravitational force and resistance to hydraulic pressure means for positioning said partition in said horizontal orientation.

6. the partitioning sediment trap of claim 5 wherein said navicular partition comprises;
    material of high specific gravity;
    whereby said high specific gravity provides proportionately greater response to gravitational force means to rapidly achieve horizontal orientation of said navicular partition.

7. the partitioning sediment trap of claim 5 wherein said navicular partition comprises;
    material having self-lubricating properties;
    whereby said self-lubricating properties provide low friction means for moving said navicular partition in said dispensing device.

8. the partitioning sediment trap of claim 1, wherein said automatic dispensing device comprises,
    a storage chamber for holding a plurality of said partitions;
    a movable chamber of similar planer dimension of said storage chamber constructed to contain a single said partition positioned below said storage chamber;

a release chamber generally positioned opposite said storage chamber and below said movable chamber constructed to provide similar planar dimension of said moveable chamber;

gearmotor and electrical circuit means for positioning said movable chamber below said storage chamber;

gravity means for moving single said partition from said storage chamber to said moveable chamber;

means for positioning said moving chamber containing single said partition above said release chamber;

gravity means for releasing said partition from said release chamber;

whereby said partition falls freely from said automatic dispensing device.

9. the partitioning sediment trap of claim 8 comprising;

said partitions positioned with convex surface upward in said storage chamber and said movable chamber;

a deflector positioned within said release chamber;

natural gravitational force means for striking said partition on said deflector;

whereby tilting of said partition to steep angle accelerates downward movement, increasing hydraulic pressure to rapidly stabilizes said partition in said horizontal position during descent through water.

10. the partitioning sediment trap of claim 1 wherein emplacement of said partitions in horizontal position on surface of said accumulated particles comprises;

said vertically alignable collecting tube;

said partition;

means for adjusting space between outer diameter of said partition and inner diameter of said collecting tube;

whereby upward escape of water through said space controls rate of descent of said partition in said collecting tube.

11. the partitioning sediment trap of claim 1 wherein the said elongate, vertically alignable collecting tube comprises;

transparent material;

whereby transparency provides means for inspection of undisturbed particles, textures and structures imparted by processes operating in said water body.

12. A partitioning sediment trap adapted to be positioned in a body of water comprising:

an elongate, vertically alignable, transparent collecting tube having an open upper end and a closed lower end for containing accumulated particles in said water body;

a generally funnel-shaped magnifying cone positioned with the small diameter end thereof extending into said open end of said transparent collecting tube;

navicular partitions an automatic dispensing device containing a plurality of said partitions positioned to release single said partition into said magnifying cone and said collecting tube at predetermined time intervals;

the improvement whereby means are provided by natural gravitational force and resistance to hydraulic pressure for positioning said navicular partition in a generally horizontal position on surface of said accumulated particles in said collecting tube.

13. the partitioning sediment trap of claim 12, wherein said means for emplacing said navicular partition in said horizontal orientation comprises:

a navicular partition exceeding the specific gravity of water;

a generally convex surface on one side of said partition;

a generally concave surface on opposing side of said partition;

automatic means of natural gravitational force and differential resistance of concave and convex surfaces to hydraulic pressure for achieving substantially stable horizontal orientation during descent of said navicular partition;

whereby said partition comes to rest horizontally on upper surface of said undisturbed accumulated particles in said collecting tube.

14. the partitioning sediment trap of claim 13 wherein said navicular partition comprises;

material of high specific gravity;

whereby said high specific gravity employs proportionate gravitational force means and hydraulic resistance means to provide horizontal orientation of said partition.

15. the partitioning sediment trap of claim 13 wherein said partition comprises;

material having self-lubricating properties;

whereby said self-lubricating properties provide low friction means for moving said partitions in said dispensing device.

16. the partitioning sediment trap of claim 12 wherein emplacement of said partitions in horizontal orientation comprises;

said vertically alignable collecting tube;

said navicular partition in said horizontal orientation;

means for adjusting space between outer diameter of said partition and inner diameter of said collecting tube;

whereby upward escape of water through said space slows rate of descent of said partition in said collecting tube.

17. the partitioning sediment trap of claim 12 wherein the said elongate, vertically alignable collecting tube comprises;

transparent material;

whereby transparency provides means for inspection of undisturbed particles, textures, and structures imparted by processes operating in said water body.

18. the partitioning sediment trap of claim 12, wherein said automatic dispensing device comprises, a storage chamber for holding a plurality of said partitions;

a movable chamber positioned below said storage chamber, constructed to contain a single said partition;

a release chamber positioned below and laterally offset to said storage chamber;

means for positioning said movable chamber containing single said partition above said release chamber;

whereby said partition falls freely from said automatic dispensing device.

19. the partitioning sediment trap of claim 18 comprising;

said partition with said concave surface positioned upward in said moving chamber;

said partition with opposing convex surface positioned downward in said moving chamber;

hydraulic pressure means for maintaining said convex surface positioned downward during descent of said partition in said magnifying cone and said collecting tube.

20. A partitioning sediment trap adapted to be positioned in a body of water comprising:

an elongate, vertically alignable, transparent collecting tube having an open upper end and a closed lower end for containing accumulated particles in said water body;

a generally funnel-shaped magnifying cone positioned with the small diameter end thereof extending into said open end of said transparent collecting tube;

a plurality of planar partitions exceeding specific gravity of water;

an automatic dispensing device positioned within magnifying cone and constructed to release single said partitions into said magnifying cone and said collecting tube at predetermined time intervals;

the improvement whereby means are provided for isolating said accumulated particles between generally horizontal solid partitions in said collecting tube.

* * * * *